US012579907B2

(12) United States Patent
Vitagliano

(10) Patent No.: US 12,579,907 B2
(45) Date of Patent: Mar. 17, 2026

(54) MEDICAL TRAINING DEVICE AND METHOD TO USE IT IN TEACHING LAPAROSCOPIC AND ROBOTIC PARTIAL NEPHRECTOMY

(71) Applicant: Gonzalo Juan Vitagliano, Fort Lauderdale, FL (US)

(72) Inventor: Gonzalo Juan Vitagliano, Fort Lauderdale, FL (US)

( * ) Notice: Subject to any disclaimer, the term of this patent is extended or adjusted under 35 U.S.C. 154(b) by 1273 days.

(21) Appl. No.: 17/304,375

(22) Filed: Jun. 20, 2021

(65) Prior Publication Data

US 2022/0406221 A1 Dec. 22, 2022

(51) Int. Cl.
*G09B 23/30* (2006.01)
*A61B 34/30* (2016.01)
*G09B 9/00* (2006.01)

(52) U.S. Cl.
CPC .............. *G09B 23/30* (2013.01); *A61B 34/30* (2016.02); *G09B 9/00* (2013.01)

(58) Field of Classification Search
CPC ........ G09B 23/30; G09B 9/00; G09B 23/285; A61B 34/30
See application file for complete search history.

(56) References Cited

U.S. PATENT DOCUMENTS 4,493,653 A * 1/1985 Robbins ............... G09B 23/286
434/218
5,014,686 A 5/1991 Schafer

| 5,055,051 A | 10/1991 | Duncan |
|---|---|---|
| 7,837,473 B2 | 11/2010 | Koh |
| 7,997,903 B2 | 8/2011 | Hasson |
| 8,460,002 B2 | 6/2013 | Wang |
| 9,564,068 B2 | 2/2017 | Redaelli |
| 9,734,732 B2 | 8/2017 | Jabbour |
| 9,786,202 B2 | 10/2017 | Huang |
| 10,413,374 B2 | 9/2019 | Chassot |
| 10,573,201 B2 | 2/2020 | Tian |
| 10,702,237 B2 | 7/2020 | Kirby |

(Continued)

FOREIGN PATENT DOCUMENTS

EP 2797068 B1 8/2020

OTHER PUBLICATIONS

Roslyn Rags, "How to dilute "tie dye" dye [Tips]" Jun. 22, 2015, available at https://www.youtube.com/watch?v=aSoPTP9Lao4 (Year : 2015).*

(Continued)

*Primary Examiner* — Kang Hu
*Assistant Examiner* — Anthony James Bulthuis

(57) ABSTRACT

The present application discloses and claims a kidney phantom consisting of a silicone rubber model featuring the anatomical shape of a human kidney, the renal artery, the renal vein, and a total of 11 tumors and 2 cysts. Each tumor is represented by a solid mass, while cysts are empty three-dimensional shapes. In order to accommodate the needs of both novice and advanced surgeons, tumors were designed with increasing surgical difficulty. The kidney phantom disclosed in the present application can be combined with a commercially available ensemble of laparoscopic tools to provide localized and remote training to surgeons and medical staff practicing laparoscopic and robotic partial nephrectomy.

4 Claims, 9 Drawing Sheets

(56)                 References Cited

U.S. PATENT DOCUMENTS

| | | | |
|---|---|---|---|
| 2012/0015339 A1* | 1/2012 | Hendrickson | G09B 23/30 |
| | | | 434/273 |
| 2016/0148541 A1 | 5/2016 | Ristolainen | |
| 2018/0053441 A1 | 2/2018 | Slanda | |
| 2018/0225991 A1 | 8/2018 | Pedroso | |
| 2019/0122581 A1 | 4/2019 | Munro | |
| 2019/0147767 A1 | 5/2019 | Hofstetter | |
| 2019/0172370 A1 | 6/2019 | Ormond | |
| 2019/0239972 A1 | 8/2019 | Chassot | |
| 2019/0328473 A1 | 10/2019 | Chassot | |

OTHER PUBLICATIONS

Atsuhiko Ochi; Satoru Muro; Takuya Adachi; Keiichi Akita; Zoning inside the renal fascia: The anatomical relationship between the urinary system and perirenal fat; Jul. 27, 2020; International Journal of Urology; 625-633 (Year: 2020).*
Ristolainen, Economically affordable anatomical kidney phantom with calyxes for puncture and drainage training in interventional urology and radiology, Acta Radiologica Short.
Adams, Soft 3D-Printed Phantom of the Human Kidney with Collecting System, Annals of Biomedical Engineering.
Bluephantom—Replacement Kidney for Renal Biopsy Ultrasound Model.
Dargahi, Fabrication, Characterization and Modeling of Magnetorheological Elastomers.
Davis, Feasibility of a Touch Sensitive Breast Phantom for Use in the Training of Physicians in Clinical Breast Examination.
Melnyk, Mechanical and functional validation of a perfused, robot-assisted partial nephrectomy simulation platform using a combination of 3D printing and hydrogel casting, Wor.
Parsons, Renal Nephrometry Scoring System: The Radiologist's Perspective, Genitourinary Imaging • Clinical Perspective.
urotrainer.com Retrieved on Jun. 13, 2021.
Vitagliano, G. Surgical Simulator for Laparoscopic Partial Nephrectomy for Renal Cell Carcinoma Retrieved from: https://www.urotoday.com/video-lectures/endourology-today/video.
Vitagliano, G. Retrieved from https://twitter.com/DrVitagliano.

\* cited by examiner

6

28

6

|    | RENAL Score | Tumor Size |
|----|-------------|------------|
| 21 | 4a          | 15mm       |
| 22 | 10xh        | 20mm       |
| 23 | 7xh         | 15mm       |
| 24 | 4a          | 15mm       |
| 25 | 7x          | 35mm       |
| 26 | 7a          | 35mm       |
| 27 | 9x          | 15mm       |
| 28 | 4p          | 15mm       |
| 29 | 5p          | 15mm       |
| 30 | 7p          | 16mm       |
| 31 | 4p          | 15mm       |

FIGURE 6

MEDICAL TRAINING DEVICE AND METHOD TO USE IT IN TEACHING LAPAROSCOPIC AND ROBOTIC PARTIAL NEPHRECTOMY

STATEMENT REGARDING FEDERALLY SPONSORED RESEARCH OR DEVELOPMENT

The present patent application did not benefit by any form of funding sponsored by the United States government.

BACKGROUND OF THE INVENTION

The present invention relates to surgical training, and particularly to a structure for use in learning laparoscopic and robotic surgical techniques.

With advancements in modern medicine minimally invasive, laparoscopic, and robotic surgeries become more and more common. Laparoscopic surgery is a technique belonging to the field of the medical arts in which narrow tubes known as trocars are inserted into the human body through small incisions, often smaller than one centimeter. Through these trocars, long, narrow instruments are inserted. The surgeon uses these instruments to manipulate, cut, and sew tissue. In the field of urology laparoscopic surgery is the standard procedure for the removal of a kidney or a portion of it. This kind or medical procedure is called nephrectomy. Nephrectomy can be either total, when the entire kidney is removed, or partial, when only a portion of the kidney is removed.

There are several reasons to perform a nephrectomy including removing a tumor or a cyst. A partial nephrectomy is indicated, for example, when a patient already underwent through a total nephrectomy and only has one kidney. One problem with partial laparoscopic nephrectomy is that requires years of training to be mastered. Training can be achieved practicing on cadavers or kidneys harvested from pigs, or it can be achieved by using a phantom organ.

A number of devices have been developed to reproduce a kidney for different reasons. For example, European published patent application E.P. 2,797,061B1 to Asko Ristolainen discloses an anatomical kidney phantom simulator for radiological training comprising a housing filled with surrounding material replicating soft tissue of a patient, and covered with a covering material having properties corresponding to the patient skin, an anatomical kidney phantom corresponding to the patient kidney placed into the surrounding material and having number of cavities simulating kidney calyxes, where each of the cavities is separated from one another. The patient specific anatomical kidney phantom simulator of the Ristolainen invention further comprises outer reservoirs wherein each outer reservoir is filled with a corresponding liquid of a different color or x-ray opaque contrast liquid in the anatomical kidney phantom of the patient and each of the outer reservoirs are separated from one another and fixed to the housing of the anatomical kidney phantom simulator, channels in the surrounding material for connecting the cavities with the outer reservoirs for introducing different colors or x-ray opaque contrast liquids from outer reservoirs into the cavities simulating the kidney calyxes of the patient, connecting pipes for connecting the channels with the outer reservoirs where each outer reservoir is connected by corresponding pipe and channel only to one cavity simulating kidney calyxes, wherein the cavities simulating kidney calyxes are formed from air balloons with diameter 5 to 7 mm which are placed into the mold before casting the anatomical kidney phantom and removed after casting.

In addition to that U.S. Pat. No. 5,014,686 to Schafer discloses and claims a phantom kidney stone system for use with a commercial lithotripsy system includes a phantom kidney stone which simulates a human kidney stone and is suspended into the field of operation of the commercial lithotripsy system. The system described in the Schafer patent also includes a trigger which is connected to receive a shock wave signal from the lithotripter which is representative of a shock wave output from the lithotripter. The trigger generates a trigger signal in response to the signal from the lithotripter.

In the field of medical training devices U.S. Pat. No. 8,460,002 to Wang et al. directed to a laparoscopic trainer and method of training discloses and claims a surgical training device for the practice of laparoscopic surgery comprising a base and a face wall extending from a side of said base such to block direct visualization of the operation area from the normal external position of the eyes of the trainee using the device. The face wall comprising a front wall and an upper wall. The front wall extending upwardly from the base; the upper wall is then extended upwardly and inwardly from the front wall. A flexible membrane is stretched on upper wall and has at least two portals such that adaptors can be inserted on flexible membrane. The adaptors are further fitted with stoppers to prevent adaptors been pulled out from the membrane during training. The surgical instruments can pass through the openings of adaptors to manipulate simulated tissue or another operable structure on the base. A plain spherical bearing set, including a bearing seat and a plain spherical bearing, is also installed on said upper wall. The bearing seat has a bearing hole to interference fit with plain spherical hearing and two bolt holes to hold bearing seat on upper wall such that a camera handle can pass through plain spherical bearing to catch the image on base.

Finally U.S. Pat. No. 10,573,201 to Tian et al., directed to a method to produce a phantom and a phantom discloses and claims a phantom that can also comprise a structure such as a tumor or kidney stone. A kidney phantom is then provided comprising the ureter, the renal pelvis and the major and minor calyxes connected thereto, as well as the renal vein and the renal artery which then branch of into the interlobular vein and the interlobular artery. The surgical training aid described in the Tian et al. patent can be connected to different fluid supplies, mimicking the function of these fluid conducting structures and a surgeon or medical student can then perform e.g. tumor removal surgery on a kidney phantom that has fluids being conducted therein. Under the teaching of the Tian et al. patent if the surgeon or medical student then severs one of these structures a fluid will leak from the kidney phantom and will then have to be blocked during the training exercise.

Despite all the efforts listed above prior art patents describe structures that are either not truly convenient or else involve complicated, expensive, and overly difficult assembly and/or disassembly parts and procedures. The medical training device and method to use it in teaching laparoscopic partial nephrectomy consist of a kidney phantom featuring a unique design combined to an ensemble of communication devices and apparatuses allowing two-way communication between the on-site trainee and the off-site mentor. An additional improvement that distinguishes and improves the medical training device of the present application over the prior art is a specially designed kidney phantom featuring a plurality of anatomical anomalies each representing a tumor, or a cyst associated with a different RENAL score.

SUMMARY OF THE INVENTION

The medical training device disclosed in the present application is a kidney phantom featuring a plurality of anatomical anomalies. In one preferred embodiment of the medical training device disclosed in the instant application consists in a three-dimensional kidney phantom representing the human kidney in a one-to-one scale. The kidney phantom of the present application consists of a silicone rubber model featuring the anatomical shape of a human kidney, the renal artery, the renal vein, and a total of 11 tumors and 2 cysts. Each tumor is represented by a solid mass, while cysts are empty three-dimensional shapes. In order to accommodate the needs of both novice and advanced surgeons, tumors were designed with increasing surgical difficulty.

In another preferred embodiment of the medical training device and method to use it in teaching laparoscopic and robotic partial nephrectomy the kidney phantom is designed to be used in conjunction with a laparoscopic training box. In a further embodiment of the medical training device and method to use it in teaching laparoscopic partial nephrectomy the kidney phantom is designed to be used to train surgeons in conjunction with a laparoscopic training box and a two way communication device where a local trainee can be guided by a remotely situated mentor or trainer.

In a further separate embodiment of the medical training device and method to use it in teaching laparoscopic and robotic partial nephrectomy the kidney phantom is designed to be used to train surgeons in conjunction with a laparoscopic training box and a multiple way communication device where a local trainee can be guided by a remotely situated mentor or trainer and where the training procedure can be observed by a plurality of remotely located observers.

It is then the principal object of the present application is to provide for a medical training device that allows surgeons to practice partial laparoscopic and robotic nephrectomy on a kidney phantom representative the human kidney without having to explant one from a cadaver or without having to practice on a live patient. It is a secondary objective of the present invention to provide a that system allows medical students to receive feedback in real time.

It is an additional objective of the present invention to provide a device and a method that allow students and trainers to interact from remote location. It is a final objective of the present invention to provide for a device that is relatively inexpensive and easy to build and set up and disassemble for easy storage and transportation, but can eventually be sold at a premium.

These and other objective achieved by the device of the present invention will be apparent by the drawings, by their detailed description, by the specification, and by the claims here from appended.

BRIEF DESCRIPTION OF THE DRAWINGS

FIG. 6 is summary of the RENAL scores of the tumors featured in one of the preferred embodiments of the kidney phantom disclosed in the present application.

DETAILED DESCRIPTION OF THE DRAWINGS

Figure 1:
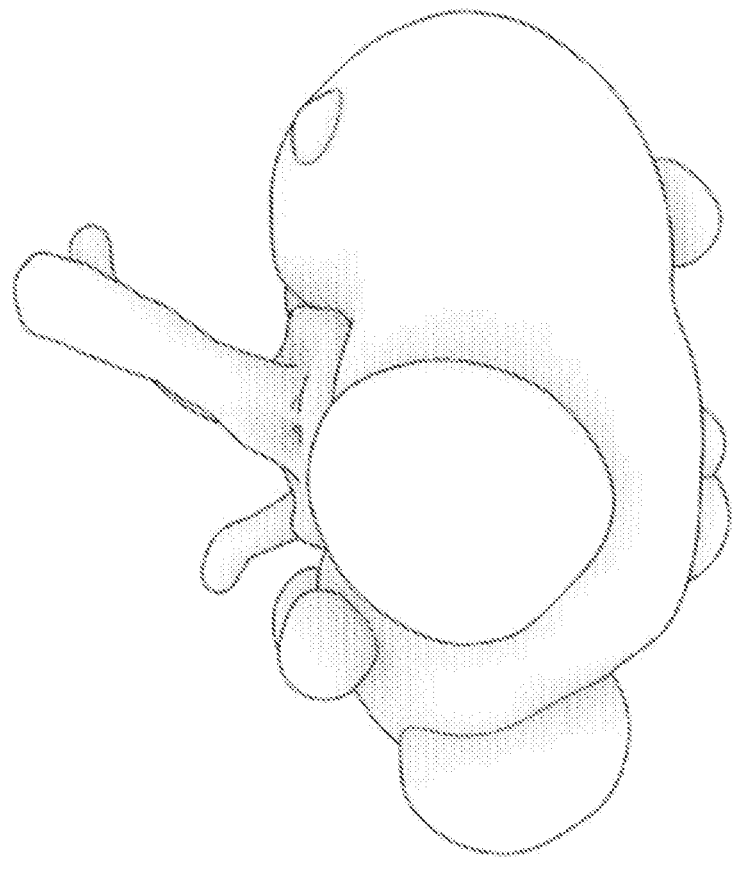
FIG. 1 is a pictorial representation of a first perspective view of the kidney phantom featuring several anatomical anomalies object of the present application.

A first object of the present application consists in a kidney phantom (1) for training in the laparoscopic resection of kidney tumors that comprises: a first outermost layer (2) representing the fascia, a second middle layer (3) representing the perineal fat capsule, a third interior body (4) representing the parenchyma, a plurality of tubular connectors (5) representing the renal arteries and the renal veins, and a plurality or anatomical anomalies (6).

In a first preferred embodiment of the kidney phantom of the instant application said first outermost layer representing the fascia is made of platinum-catalyzed silicone rubber mixed with white dye. Silicone rubber is an elastomer (rubber-like material) composed of silicone—itself a polymer—containing silicon together with carbon, hydrogen, and oxygen. Silicone rubbers are used in industry, and there are multiple formulations. Silicone rubbers are often one- or two-part polymers, and may contain fillers to improve properties or reduce cost. Silicone rubber is generally non-reactive, stable, and resistant to extreme environments and temperatures from −55 to 300° C. (−70 to 570° F.) while still maintaining its useful properties.

In its uncured state, silicone rubber is a highly adhesive gel or liquid. In order to convert to a solid, it must be cured, vulcanized, or catalyzed. This is normally carried out in a two-stage process at the point of manufacture into the desired shape, and then in a prolonged post-cure process. It can also be injection molded. Silicone rubber may be cured by a platinum-catalyzed cure system, a condensation cure system, a peroxide cure system, or an oxime cure system. For the platinum-catalyzed cure system, the curing process can be accelerated by adding heat or pressure. In a platinum-based silicone cure system, also called an addition system (because the key reaction-building polymer is an addition reaction), a hydride- and a vinyl-functional siloxane polymer react in the presence of a platinum complex catalyst, creating an ethyl bridge between the two. The reaction has no byproducts. Such silicone rubbers cure quickly, though the rate of or even ability to cure is easily inhibited in the presence of elemental tin, sulfur, and many amine compounds. The density of the silicone rubber platinum cured of the present application is on or about 1.07 [g cm$^{-3}$]=1,070 [kg m$^{-3}$].

The silicone rubber of the present application can be obtained by mixing several commercial products including a silicone rubber mix having a viscosity of 3,000 [centipoise]=3 [Pa s] with a silicone tactile mutator having a viscosity of 10,000 [centipoise]=10 [Pa s]. In the specific the component of the kidney phantom (1) may be made as follow: (a) structures representing the tumors, cysts, arteries, veins and ureter: 100% silicon rubber platinum cured; (b) body of the kidney phantom representing the parenchyma: 90% silicon rubber platinum cured and 10% silicone tactile mutator; (c) fat tissue: 74% silicon rubber platinum cured and 26% silicone tactile mutator. The silicone tactile mutator of the present application is a compound characterized by a density of 0.94 and 1 [g cm$^{-3}$]=940 and 1,000 [kg m$^{-3}$].

An example of a commercially available silicon rubber platinum cured is ECOFLEX 00-30 (RT). An example of a commercially available silicone tactile mutator is SLACKER (RT). Both ECOFLEX 00-30 (RT) and SLACKER (RT) are Trademarks registered with the United States Patent and Trademark office, belonging to Smooth-On Inc. a Pennsylvania corporation located in 5600 Lower Macungie Road Macungie 18062 PENNSYLVANIA and will not be used in any disparaging or derogatory way in the present application.

The kidney phantom (1) described in the instant application also features colors to add an additional element of reality. For example, the kidney phantom of the present application may have said second middle layer representing the perineal fat capsule made of platinum-catalyzed silicone rubber mixed with water, a red dye, and a yellow dye; said third interior body representing the parenchyma made of platinum-catalyzed silicone rubber mixed with red dye. The anatomical anomalies represent a kidney tumor (7) constituted by a hard center (8), and a surrounding tissue (9).

The anatomical anomalies represent a renal cyst (10) constituted by an empty pouch (11) enclosed by a surrounding tissue (12). In a separate preferred embodiment of the kidney phantom of the present application said empty pouch (11) is filled up with water. A separate preferred embodiment of the kidney phantom described in the instant application was based on the experience gained by the inventor in performing laparoscopic and robotic partial nephrectomies. A three-dimensional kidney phantom of size representative of the one of an adult patient was realized with a silicone rubber platinum cured. The model was designed with a total of eleven tumors and two cysts. With reference to FIG. 2, FIG. 3, FIG. 4 and FIG. 5 the individual identity of each anatomical anomaly corresponding to a different renal score is described. Anatomical anomaly (21) represents an individual tumor of size 15 [mm]=1.5×10$^{-2}$ [m] associated with a renal score of 4a. Anatomical anomaly (22) represents an individual tumor of size 20 [mm]=2.0×10$^{-2}$ [m], close to a main renal vein or artery associated with a renal score of 10Xh. Anatomical anomaly (23) represents an individual tumor of size 15 [mm]=1.5×10$^{-2}$ [m] associated with a renal score of 7h. Anatomical anomaly (24) represents an individual tumor of size 15 [mm]=1.5×10$^{-2}$ [m] associated with a renal score of 4a. Anatomical anomaly (25) represents an individual tumor of size 35 [mm]=3.5×10$^{-2}$ [m] associated with a renal score of 7x. Anatomical anomaly (26) represents an individual tumor of size 35 [mm]=3.5×10$^{-2}$ [m] associated with a renal score of 7a. Anatomical anomaly (27) (not shown in the drawing as it is internal) represents an individual tumor of size 15 [mm]=1.5×10$^{-2}$ [m] associated with a renal score of 9x. Anatomical anomaly (28) represents an individual tumor of size 15 [mm]=1.5×10$^{-2}$ [m] associated with a renal score of 4p. Anatomical anomaly (29) represents an individual tumor of size 15 [mm]=1.5×10$^{-2}$ [m] associated with a renal score of 5p. Anatomical anomaly (30)

represents an individual tumor of size 16 [mm]=1.6×10$^{-2}$ [m] associated with a renal score of 7p. Anatomical anomaly (31) represents an individual tumor of size 15 [mm]=1.5×10$^{-2}$ [m] associated with a renal score of 4p.

The RENAL nephrometry scoring system was developed to categorize renal masses into low, intermediate and high complexity, based on cross-sectional imaging findings. Its purpose is to aid in decision making, patient counseling, surgical planning, and patient follow-up, as well as academic reporting. RENAL is actually an easy-to-remember acronym of the five features scored. RENAL stands for Radius, Exophytic, Nearness, Anterior, and Location. With respect to the Radius (maximum diameter) in any axis: 1 point is assessed if the tumor is smaller than 4 [cm]=smaller than 4λ10$^{-2}$ [m]. If the radius of the tumor is in between 4 and 7 [cm] (in between 4×10$^{-2}$ and 7×10$^{-2}$ [m]) then 2 points are assessed. Three points are assessed if the tumor has a radius longer than 7 [cm]=7×10$^{-2}$ [m].

With respect to the Exophytic or endophytic tumor location: 1 point is assessed if the location is ≥50% exophytic; 2 points are assessed if the location is <50% exophytic; and 3 points are assessed if the location is 100% endophytic. The term Exophytic is used to describe an abnormal growth that stick outs from the surface of a tissue. This pattern of growth can be seen when the tissue is examined under a microscope. Pathologists use the word exophytic to describe both benign (non-cancerous) growths and malignant tumors (cancers). The term endophytic: is used to describe tumors tending to grow inward into tissues in fingerlike projections from a superficial site of origin.

With respect to the nearness to the renal collecting system or renal sinus measured in millimeters (mm) (10$^{-3}$ meters) as the shortest distance from the deepest point of the tumor if the distance is ≥7 [mm] or 7×10$^{-3}$ [m] then one point is assessed. If the distance is longer than 4 [mm] or 4×10$^{-3}$ [m] but less than 7 [mm] or 7×10$^{-3}$ [m], then 2 points are assessed. If the distance is less than 4 [mm] or 4×10$^{4}$ [m] than 3 points are assessed. Anterior or posterior location is on the axial view no points are allocated rather the descriptors: "a" (anterior), "p" (posterior) or "x" (neither) are used. Location relative to the renal poles if the tumor is entirely below the inferior pole or above the superior pole then one point is assessed. If the mass of the tumor crosses the polar line: then two points are assessed. If more than half of the mass of the tumor lies across the polar line or is entirely between the polar lines or crosses the axial midline: then three points are assessed. Small cap h is the assigned as a suffix if the mass touches the main renal artery or vein. The sum of the points qualified by the suffixes constitutes the RENAL score of a kidney tumor.

The kidney phantom (1) was designed to address the training needs of both novice and advanced surgeons, tumors were designed with increasing surgical difficulty. The kidney phantom (1) was manufactured utilizing a base mix of silicone rubber with additives. Each tumor was designed with its own vascular supply. Specific material density was utilized in order to mimic adequate tissue density and resistance and we tested the models for compression and stretch. Renal parenchyma, tumor tissue, vascular structures and renal fat all have an individual and distinctive feel which the model is able to mimic successfully.

The simulator is made of different combination of silicone rubbers and additives that mimic the mechanical properties of the arteries, veins, tumors, ureter, cysts, fat and parenchyma. Each of this silicone rubber combinations have to be placed in the exact position in order to allow the model to look and feel as a real kidney. To achieve this, we developed a complex set of molds that give the shape of every structure before the rubber silicone is poured and cured. These molds were digitally developed and then printed in a three-dimensional (3D) printer for their later use. With the purpose of greater realism, we tested the models for compression and stretch. The mean tissue compression in a separate preferred embodiment of kidney phantom (1) designed VK-1 Urotrainer was 24.0±1.7 [kPal] and the tissue stretch was 70.0±4.5 [kPa]. The final result is a 270 [gr]=0.27 [kg] with dimensions of 120 [mm]×90 [mm]×70 [mm] model with 11 tumors and 2 cysts completely surrounded by fat. The model is fully operable with increasing levels of complexity warranting different skill level proficiency.

The kidney phantom (1) designed as described above can be at the basis of a medical training apparatus for training in the laparoscopic resection of kidney tumors comprising a base element (13) comprising a rectangular horizontal base (14), a vertical transparent rectangular wall (15) departing from said rectangular horizontal base, and an inclined support stand (16) departing from said vertical transparent rectangular wall, where said inclined support stand (16) has a plurality of holes (17) representing the laparoscopic portals, a kidney phantom (1), a plurality of trocars (18) to be inserted into the laparoscopic portals (17), a plurality of surgical laparoscopic instruments (19) to be inserted into the kidney phantom through the trocars (18), a plurality of cameras (20) connected to a central processing unit (CPU) (32) by a first plurality of connections (33), where said central processing unit (32) is further connected to a plurality of input devices (33), a plurality of output devices (34), and a power source (35), via a second plurality of connections (36).

In a separate preferred embodiment of the medical training apparatus of the present application said plurality of input devices (33) includes a microphone. Said plurality of output devices (34) includes a connection with the world wide web. Said first plurality of connections (33) includes cables and wires or it may be wireless. Similarly said second plurality of connections (36) includes cables and wires or may be wireless.

The medical training apparatus for training in the laparoscopic resection of kidney tumors may be adapted to teach robotic laparoscopic partial nephrectomy. The advantages of laparoscopic surgery—and, really, any minimally-invasive option—are mostly related to having small incisions rather than one large one: there's less blood loss, less pain and less noticeable scars. There are also economic benefits: a shorter hospital stay generally means lower medical costs, and a faster recovery means you can get back to work sooner. Laparoscopic surgery does have some limitations, however: the video images associated with it are two dimensional. And the tools can have a limited range of motion—up and down and side to side—which can make it difficult to work in tight spaces. On the flip side, laparoscopic surgeons are able to use the familiar sensations of pressure and other tactile movements to manipulate the tools.

Robotic surgery is similar to a laparoscopic procedure in many respects: the surgeon makes several small incisions and uses a video camera and instruments to guide his or her work. The difference with robotic surgery is that the surgeon sits at a computer and uses hand controls to manipulate the robot—rather than holding and manipulating the tools themselves, as with laparoscopic surgery. And the imagery is three dimensional, high definition and magnified—all of which allow for better vision and greater precision. The other distinguishing factor is that the instruments used for robotic surgery are "wristed"—they move like a hand. This provides greater range of motion and more precision, which can mean less manipulation of tissues, less bleeding and less post-operative pain than with laparoscopic surgery.

In summary robotic surgery is similar to laparoscopic surgery in the respect that they both use small incisions, a camera and surgical instruments. However, instead of holding and manipulating the surgical instruments his or herself, during robotic surgery, your MedStar Surgeon will sit at a computer console and use controls to manipulate the robot. The console provides your surgeon with high-definition, magnified 3D images, which allow for increased accuracy and vision inside your body. Compared to traditional surgery, robotic surgery provides your surgeon with a greater range of motion and precision, which may lead to less bleeding and post-operative pain.

To adapt the medical training apparatus for training in the laparoscopic resection of kidney tumors the apparatus itself may further comprises a robotic apparatus (37) to handle said plurality of surgical laparoscopic instruments (19); a console (38) to control said robotic apparatus (37); a plurality of connections (39) in between said console (38) and said robotic apparatus (37); a second power source (40) for said robotic apparatus (37); a plurality of connections (41) to link said robotic apparatus (37) to said second power source (40), a third power source (42) for said console (38); and a plurality of connections (43) to link said console (38) with said third power source (42).

The present application further discloses and claims a method to use a medical training apparatus for training in the laparoscopic resection of kidney tumors including the steps of: assembling a simulation system having a kidney phantom (1), a central processing unit (32), a plurality of input devices (33), a base element (13), a plurality of surgical laparoscopic instruments (19), a plurality of trocars (18), and a plurality of output devices (34), a plurality of connections (33, and 36), said kidney phantom (1) comprising a plurality of anatomical anomalies (6) representing renal cysts and tumors of different renal scores; providing said simulation system along with documentation to a plurality of medical facilities; and providing training on use of said simulator, different simulations, and criteria for grading performance on said simulations, said training including team training for conducting said simulations using said simulation system, and said simulations including an laparoscopic resection of kidney tumors simulation comprising: instructing a medical staff that a patient has had a kidney tumor, wherein the patient's is the kidney phantom, instructing the medical staff that the only a partial kidney resection can be done; initiating a simulated laparoscopic resection of kidney tumors by activating a plurality of surgical instruments (19) of the simulator through the respective trocars (18); and activating the input devices (33); observing whether said medical staff performs assessment and intervention of said laparoscopic resection of kidney tumors competently through one of said output devices (34); providing a first feedback to said medical staff; ending the simulated laparoscopic resection of kidney tumors; setting up a debriefing for said medical staff; and providing a second feedback to said medical staff.

According to the method of providing medical training in the laparoscopic resection of kidney tumors a further steps could be debriefing said medical staff; and grading said medical staff based on observations and predetermined scoring criteria. Said assembling comprises assembling at least one touch-screen monitor connected to a camera focused on said kidney phantom (1). Said assembling further comprises the steps of deflating the anatomic anomalies representing a renal cyst of the air contained therein with a syringe, and inflating it with a transparent liquid selected from the group consisting of water, saline solution, and dextrose solution. At the end of the training a certification may be awarded if the score earned by said medical staff meets a certain numerical number associated with said predetermined scoring criteria.

According to the Manual of Patent Examining Procedures all units were expressed in metric units. When non-metric units were provided by the inventor they were converted or equated to metric units. Square brackets were used to signify units of measurements.

Figure 2:
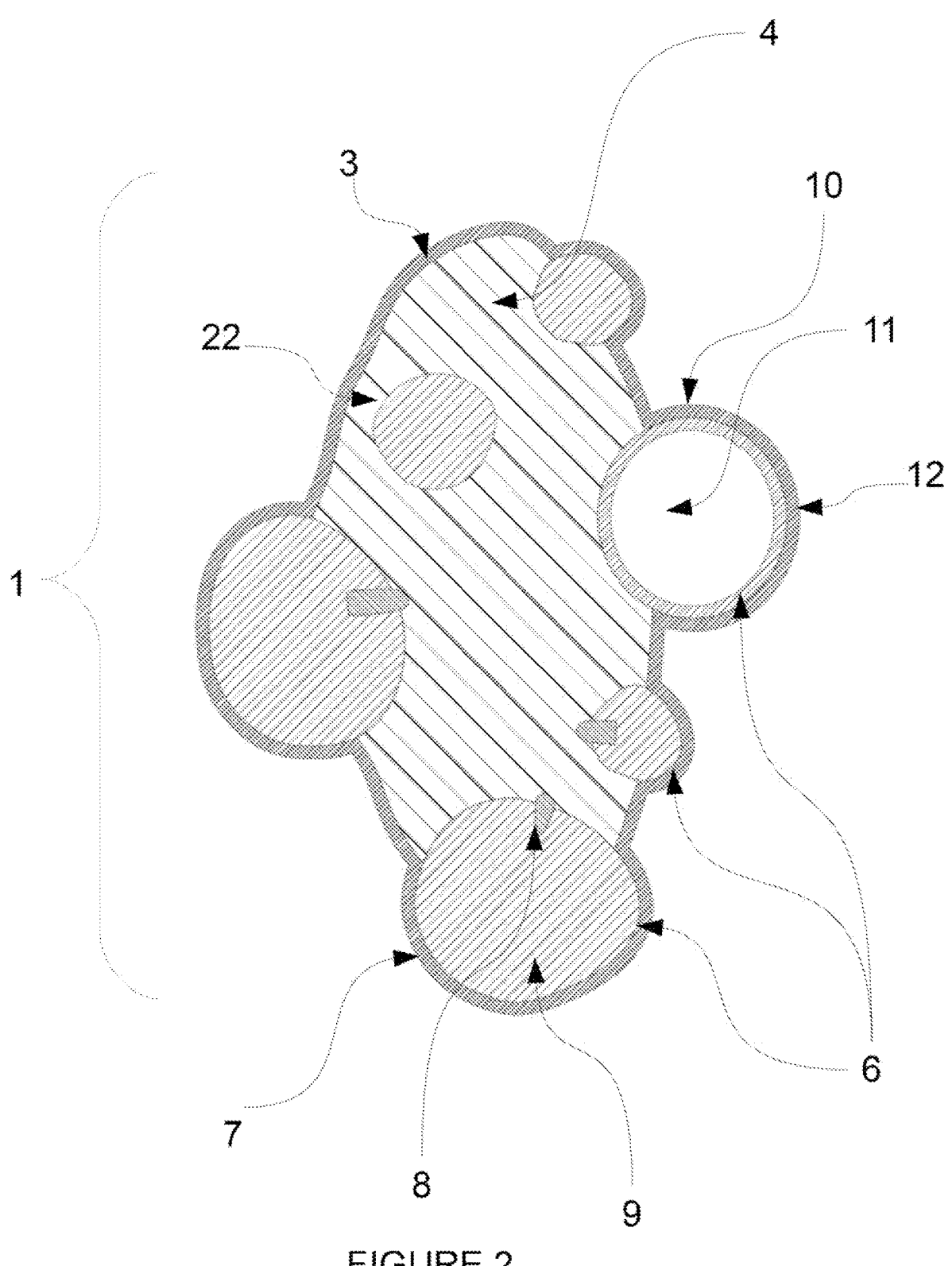
FIG. 2 is a pictorial representation of a cross sectional view of the kidney phantom featuring several anatomical anomalies object of the present application.
Figure 3:
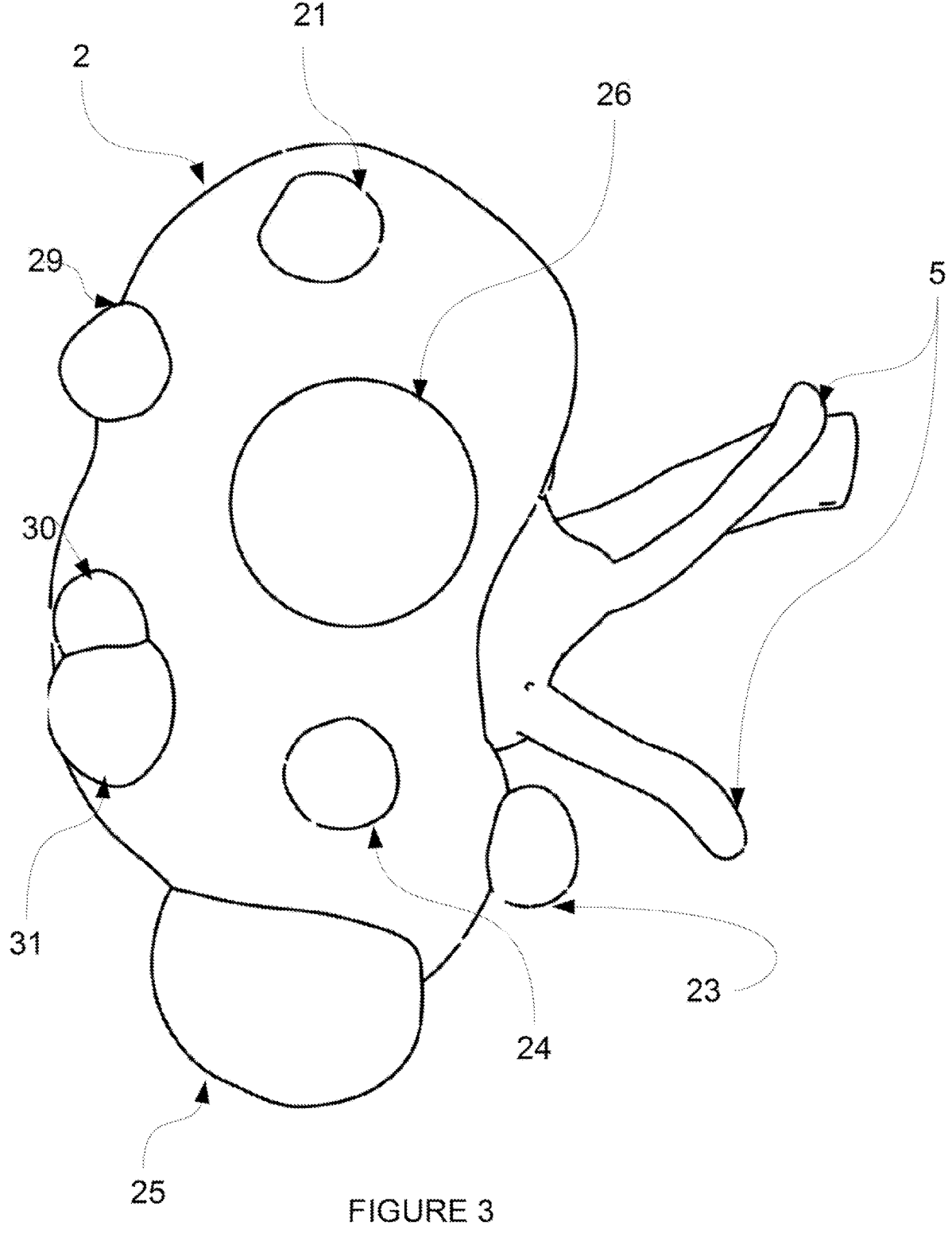
FIG. 3 is a pictorial representation of the right view of the kidney phantom featuring several anatomical anomalies object of the present application.
Figure 4:
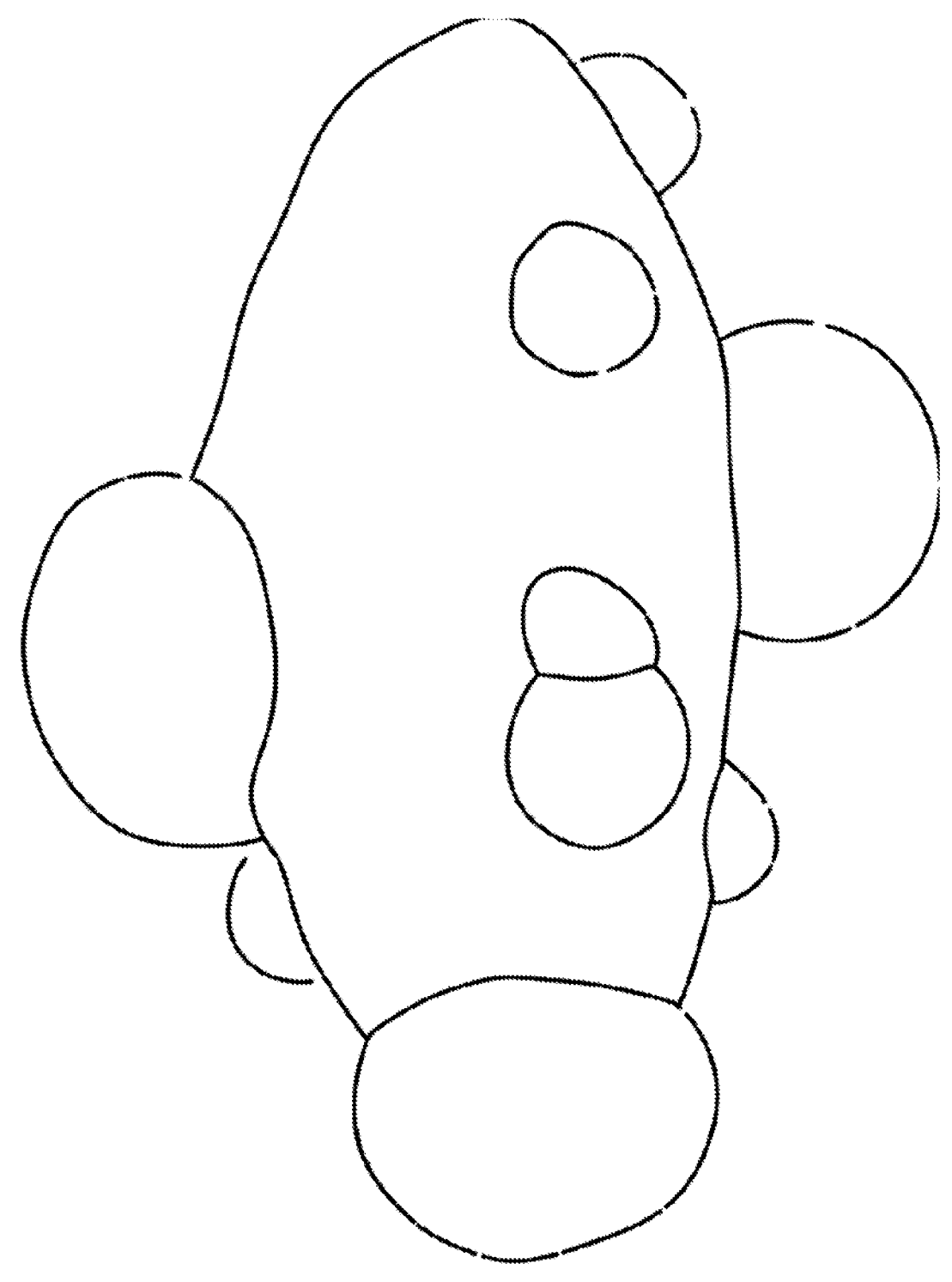
FIG. 4 is a pictorial representation of the front view of the kidney phantom featuring several anatomical anomalies object of the present application.
Figure 5:
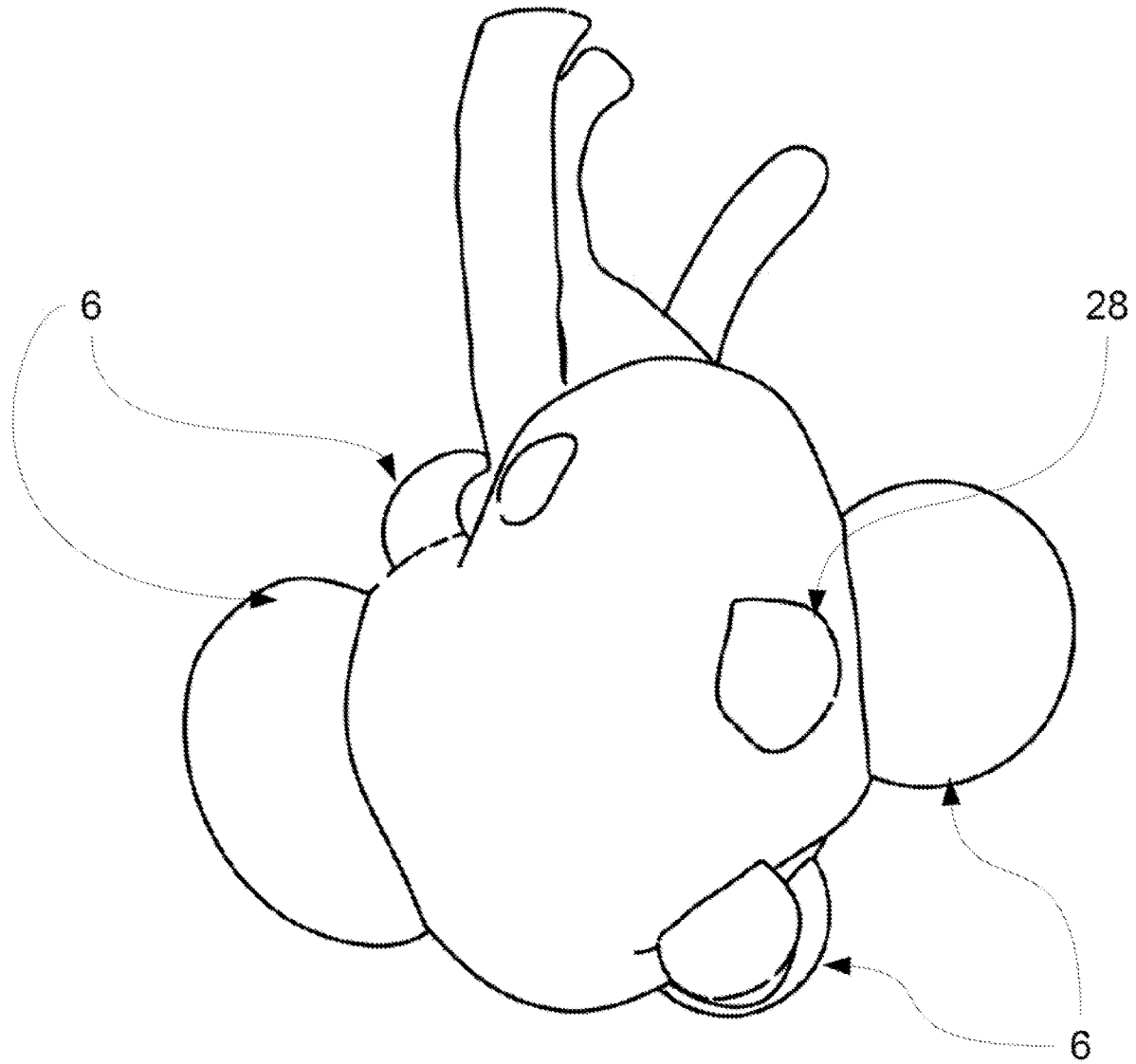
FIG. 5 is a pictorial representation of the top view of the kidney phantom featuring several anatomical anomalies object of the present application.
Figure 7:
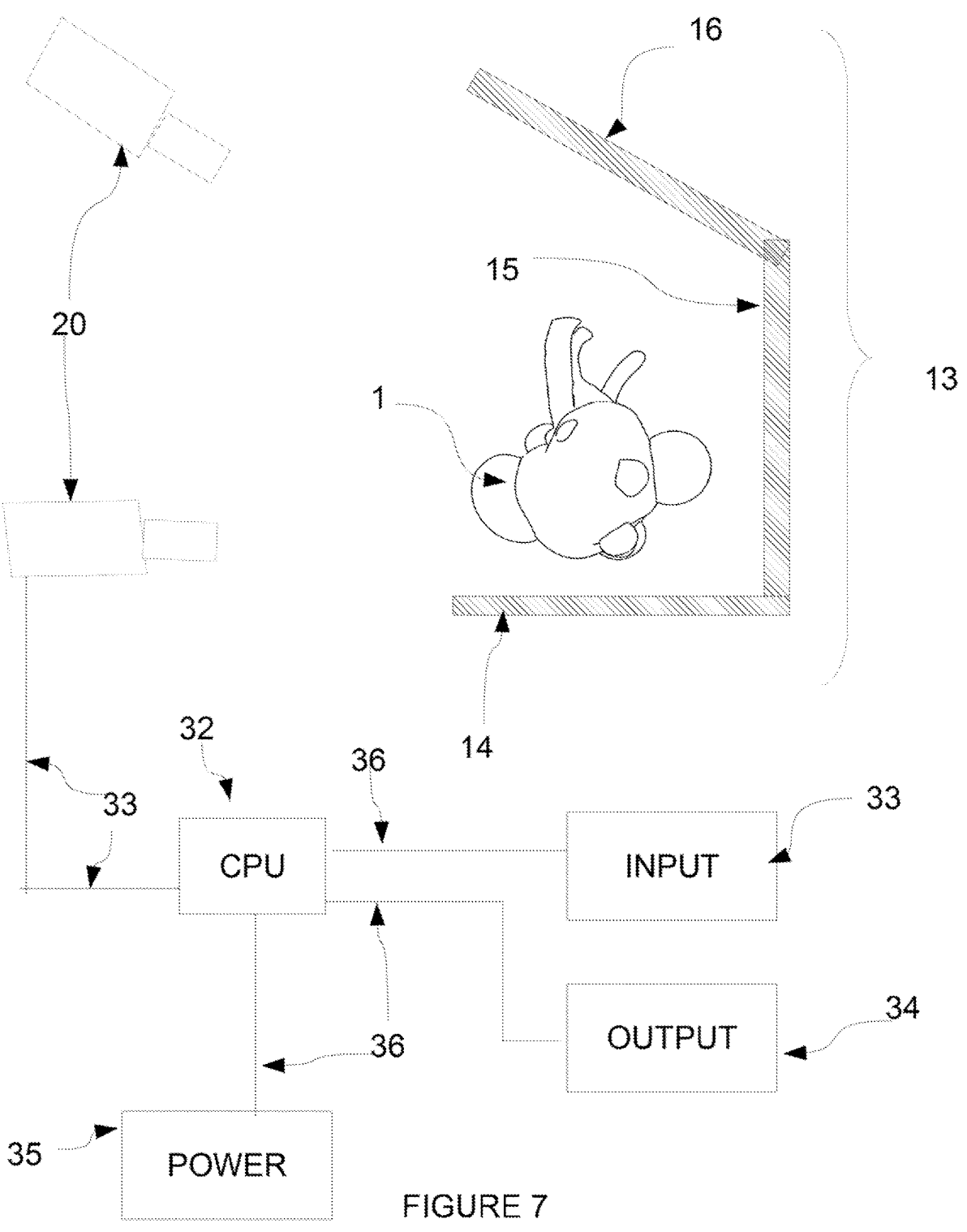
FIG. 7 is a diagrammatic representation of the medical training device used to teach partial laparoscopic and robotic nephrectomy based on kidney phantom (1) object of the present application.
Figure 8:
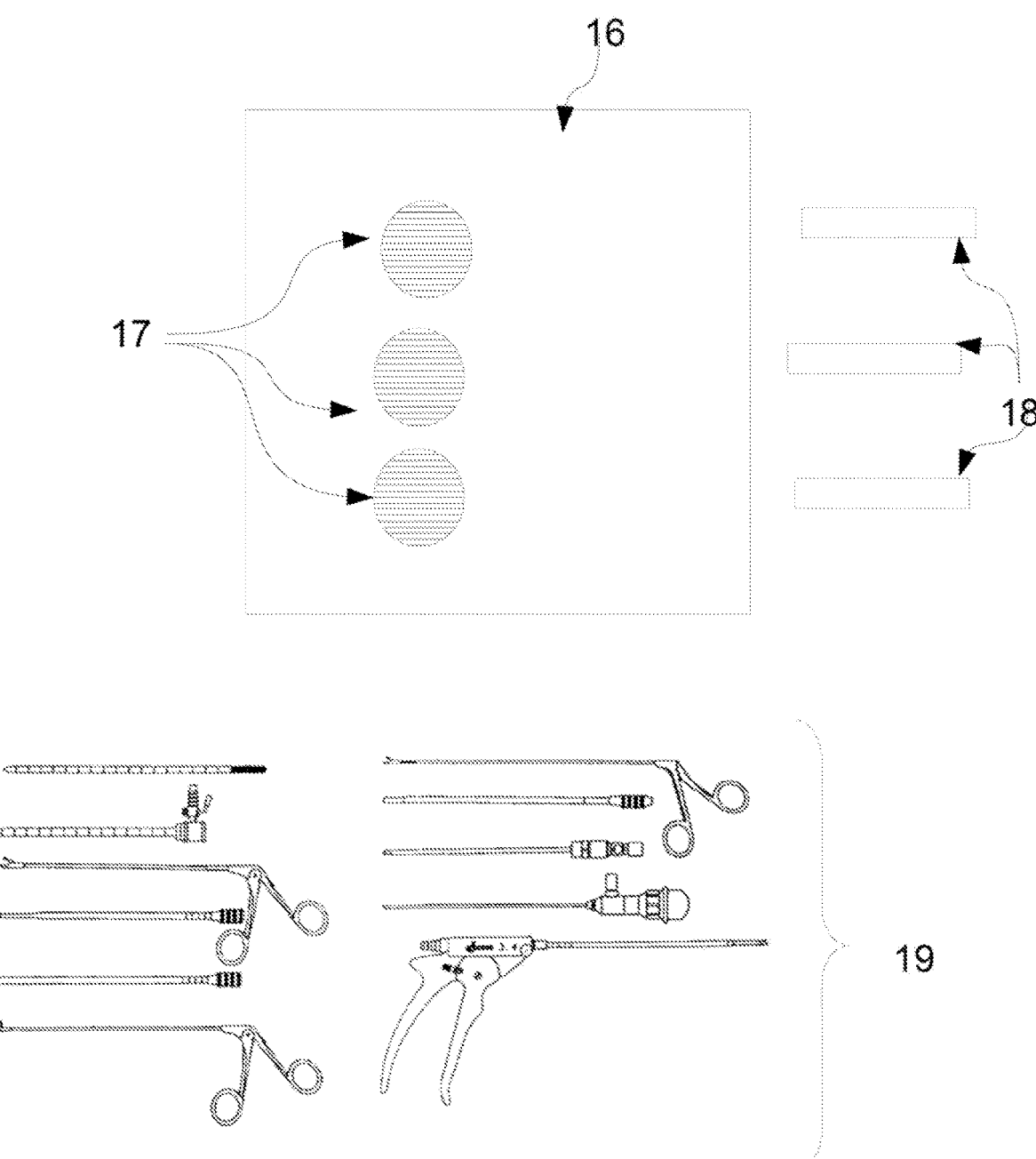
FIG. 8 is a top view of inclined support stand (16) of the base element (13) of the medical training device of the present application.
Figure 9:
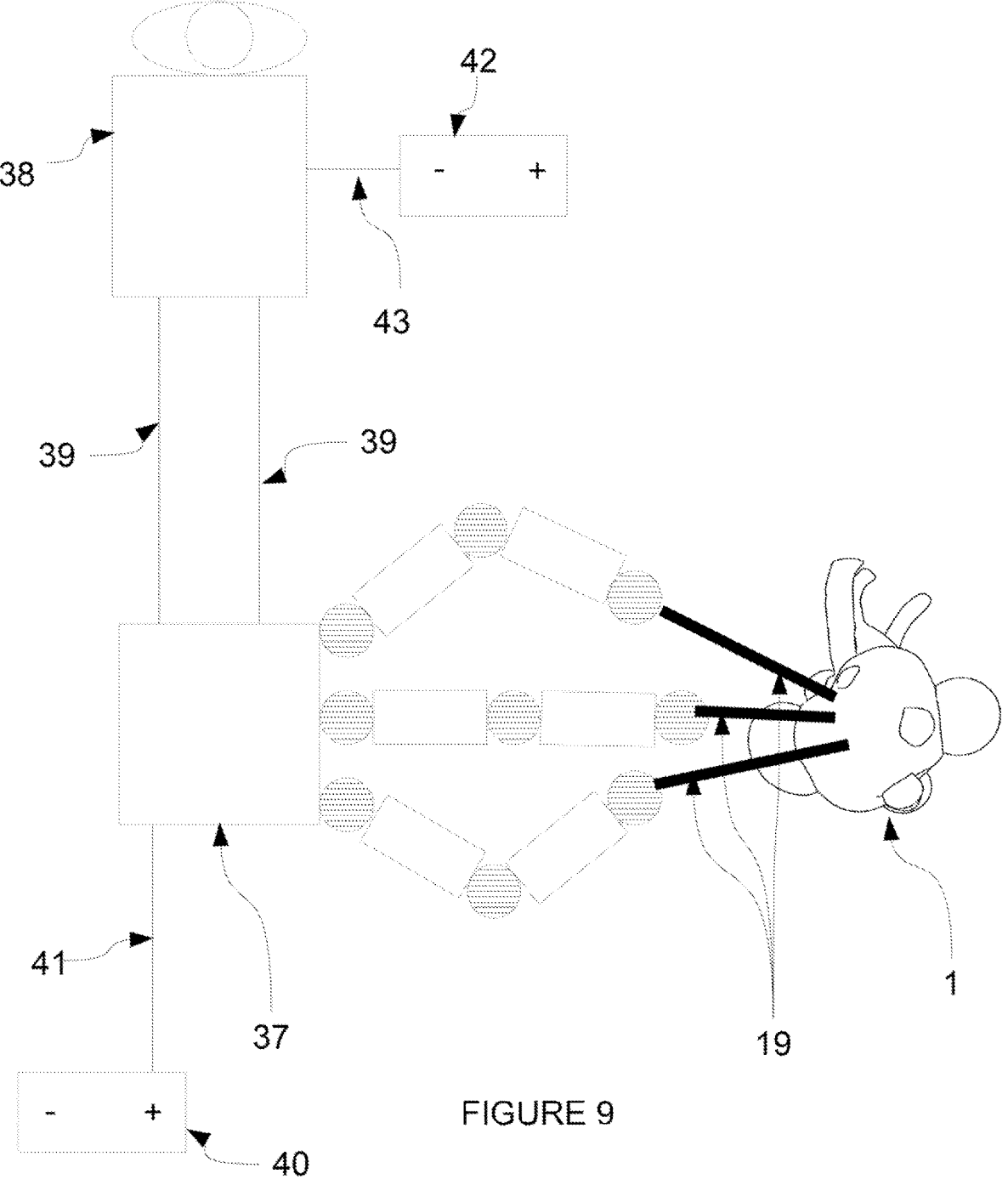
FIG. 9 is a diagrammatic illustration of one of the preferred embodiments of the medical training device of the present application featuring the use of a robotic apparatus to perform the partial nephrectomy.

Referring now to FIGS. 1-3, showing kidney phantom of the present application. It may be sold as kit comprising its different components; and at least one set of user instructions. The kit has instructions such that functional relationships are detailed in relation to the structure of the invention (such that the invention can be used, maintained, or the like in a preferred manner). The kidney phantom (1) of the present application may be manufactured and provided for sale in a wide variety of sizes and shapes for a wide assortment of applications. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized parts, different color combinations, parts may be sold separately, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

I claim:

1. A kidney phantom for training in the laparoscopic and robotic resection of kidney tumors comprising:

a first outermost layer representing the fascia made by a combination of 90% platinum-catalyzed silicone rubber mixed with white dye having a density of 1.07 [g cm$^{-3}$], and a viscosity of 3,000 [centipoise]=3 [Pa s], and 10% a silicone tactile mutator having a density in between 0.94 and 1 [g cm$^{-3}$] and a viscosity of 10,000 [centipoise]=10 [Pa s], a second middle layer representing the perirenal fat capsule made by a combination of 74% platinum-catalyzed silicone rubber mixed with water, a red dye, and a yellow dye having a density of 1.07 [g cm$^{-3}$], and a viscosity of 3,000 [centipoise]=3 [Pa s], and 26% a silicone tactile mutator having a density in between 0.94 and 1 [g cm$^{-3}$] and a viscosity of 10,000 [centipoise]=10 [Pa s], a third interior body representing the parenchyma also made by a combination of 90% platinum-catalyzed silicone rubber mixed with red dye having a density of 1.07 [g cm$^{-3}$], and a viscosity of 3,000 [centipoise]=3 [Pa s], and 10% a silicone tactile mutator having a density in between 0.94 and 1 [g cm$^{-3}$] and a viscosity of 10,000 [centipoise]=10 [Pa s], a plurality of tubular connectors representing the renal arteries and the renal veins made by 100% platinum-catalyzed silicone rubber having a density of 1.07 [g cm$^{-3}$], and a viscosity of 3,000 [centipoise]=3 [Pa s], and a plurality of anatomical anomalies also made by 100% platinum-catalyzed silicone rubber having a density of 1.07 [g cm$^{-3}$], and a viscosity of 3,000 [centipoise]=3 [Pa s].

2. The kidney phantom of claim 1 where said anatomical anomalies represent a kidney tumor constituted by a hard center, and a surrounding tissue.

3. The kidney phantom of claim 1 where said anatomical anomalies represent a renal cyst constituted by an empty pouch enclosed by a surrounding tissue.

4. The kidney phantom of claim 3 where empty pouch is filled up with water.

\* \* \* \* \*